United States Patent
Seidel et al.

(10) Patent No.: US 6,208,815 B1
(45) Date of Patent: Mar. 27, 2001

(54) METHOD FOR DIFFERENTIATING OR DETECTING PARTICLES IN A SAMPLE BY IDENTIFYING SIGNAL SEGMENTS OF TIME-RESOLVED, OPTICAL RAW SIGNALS FROM THE SAMPLE ON THE BASIS OF SINGLE PHOTON DETECTION

(75) Inventors: Claus Seidel, Göttingen; Rolf Günther; Stefan Lüpke, both of Hamburg, all of (DE)

(73) Assignee: Evotec Biosystems AG, Hamburg (DE)

( * ) Notice: Subject to any disclaimer, the term of this patent is extended or adjusted under 35 U.S.C. 154(b) by 0 days.

(21) Appl. No.: 09/308,631

(22) PCT Filed: Nov. 27, 1997

(86) PCT No.: PCT/EP97/06622

§ 371 Date: Aug. 12, 1999

§ 102(e) Date: Aug. 12, 1999

(87) PCT Pub. No.: WO98/23942

PCT Pub. Date: Jun. 4, 1998

(30) Foreign Application Priority Data

Nov. 27, 1996 (DE) .............................. 196 49 048

(51) Int. Cl.[7] ................................................ G01N 21/00
(52) U.S. Cl. ........................................ 396/337; 356/338
(58) Field of Search ................................. 356/300, 337, 356/338; 250/458.1

(56) References Cited

U.S. PATENT DOCUMENTS 4,979,824 * 12/1990 Mathies et al. .................... 356/318

FOREIGN PATENT DOCUMENTS

WO 96/27798 * 9/1996 (WO).
96/27798 9/1996 (WO).

OTHER PUBLICATIONS

Keller et al., "Single–Molecule Fluorescence Analysis in Solution," *Applied Spectroscopy*, 50(7) :12A–32A (1996).

* cited by examiner

*Primary Examiner*—Frank G. Font
*Assistant Examiner*—Phi Natividad
(74) *Attorney, Agent, or Firm*—Jacobson, Price, Holman & Stern, PLLC (57) ABSTRACT

A method for differentiating or detecting particles in a sample in which several classes of particles may be present by identifying signal segments of time-resolved, optical raw signals from the sample on the basis of single photon detection (single pulse detection), wherein the sample contains at least two classes of particles; the sample is illuminated by a light source; the optical raw signals emitted by the sample, which are derived from at least one measuring volume element V, $V \leq 10^{-12}$ l, are detected with at least one detector unit; at least one particle generates a signal fraction during its residence in the measuring in the measuring volume element; a signal segment of the optical raw signals is determined by the particle's actively and/or passively entering and then leaving again the measuring volume element; the optical raw signals are segmented into arbitrary segments; at least one set of statistical data based on the optical raw signals is established for at least one arbitrarily chosen segment; and the at least one set of statistical data or at least one combination of several sets of statistical data is evaluated for the presence of features characteristic of the signal fraction from at least one class of particles.

19 Claims, 3 Drawing Sheets

METHOD FOR DIFFERENTIATING OR DETECTING PARTICLES IN A SAMPLE BY IDENTIFYING SIGNAL SEGMENTS OF TIME-RESOLVED, OPTICAL RAW SIGNALS FROM THE SAMPLE ON THE BASIS OF SINGLE PHOTON DETECTION

The present invention relates to a method for differentiating or detecting particles in a sample by identifying signal segments of time-resolved, optical raw signals from the sample on the basis of single photon detection according to claim 1.

The method of fluorescence correlation spectroscopy (FCS) (WO 94/16313) and other confocal fluorescence techniques, as described in the Publication WO 96/13744 and in the European Patent Application 96 116 373.0, are particularly suitable for so-called homogeneous assays on a submicroliter scale. The latter application describes a method for analyzing samples by repeatedly measuring the number of photons per defined time interval in light which is emitted, scattered and/or reflected by the particles in the sample and determining the distribution of the number of photons in the respective time intervals, characterized in that the distribution of specific brightness of the particles is determined from the distribution of the numbers of photons. In these techniques, the actual measuring volume element is less than $10^{-12}$l. The term "homogeneous assays" means analytical methods in which all reacting components remain in one measuring compartment until the signal is detected. Excess components are not preliminarily separated from the reaction mixture, in contrast to the so-called ELISA methods. The above mentioned fluorescence techniques work particularly well if labeled reagents are employed in a range of between 1 pM and 0.1 $\mu$M. However, the kinetic boundary conditions of a chemical detecting reaction which is to proceed in the seconds to minutes range for practicability require the use of labeled detector reagents in excess over an analyte in the nanomolar range and above. This frequently means a great experimental difficulty in the performance of homogeneous assays if the concentration of the resulting reaction product is less than that of the excess reagent by one or more than one order of magnitude.

Homogeneous assays with confocal measuring techniques often do not offer any possibilities to keep the excess component out of the measuring volume with simple means. Only for oppositely charged particles, methods have been described (WO 94/16313) for separating excess components from the reaction product even within a reaction volume using electric fields. Unfortunately, however, such methods are unsuitable for many diagnostic detection methods of extraordinary economical importance. In particular, this applies to, e.g., the analytics of pharmacologically important receptors, e.g., on vesicles, the interaction of which with excess free labeled ligands is to be analyzed. Viruses, bacteria, cells, beads, particle fluids (e.g., with surface-bound specific chemicals as known from combinatorial chemistry), or just large molecular aggregates, such as ribosomes, can naturally be measured only in extremely low concentrations so that the use of excess reagent is unavoidable.

For homogeneous assay methods, there have been described ways to produce optical luminescence signals only in the case when complexes between the detector reagent and the particle to be detected have been formed, despite of the use of excess labeled detector reagent. These include, e.g., the methods of scintillation proximity assay (SPA), energy transfer assay through the formation of various donor-acceptor complexes or reaction products which revert luminescence quenching.

In confocal fluorimetry, the method of cross-correlation has proven useful. In cross-correlation methods, the detector reagent, e.g., bears marker A while the particle to be detected bears marker B. Although both the signals A' from the detector reagent and B' from the particle to be detected are recorded, in cross-correlation, only those signals are employed in which both signals A' and B' are recorded in the same time interval. This is the case when a complex of the detector reagent and the particle to be detected is present. In another variant, individual molecules of the detector reagent may be labeled with either of markers A* or B*. Those methods no longer yield satisfactory results when the concentration of the excess component is different from that of the complex to be detected by more than a factor of 10.

In various signal processing methods, there has been the problem of separating signals from the background noise. To solve it, the use of spectral filtering, lock-in and coincidence techniques, for example, has proven useful.

Spectral filtering is often easily done with optical signals. Thus, for example, in confocal microscopy or fluorescence correlation spectroscopy, the fluorescence signal is separated from the scattered light and the Raman emission from the solvent by using interference or colored glass filters. Wherever possible, the signal is resolved into a spectrum using a prism or grating. In many cases, however, this kind of filtering is unsufficient. For recording a complete spectrum, higher light intensities are necessary to obtain a minimum statistical base over the spectral range. Single particles, especially single molecules, are often not emitting enough photons, however. Although filters limit the spectrum to be measured, they require a detectable spectral difference.

The filtering of the signal after electric conversion into counts using fast Fourier transformation (FFT) requires assign-ability of the signal to frequencies. Correspondingly poor is the filtering performance of FFT and related techniques in analyzing the emission of particles the movement of which is random because of diffusion rather than regularly. Lock-in techniques also require a periodic signal as the base signal.

Coincidence techniques require a second signal as a trigger signal. Such a signal is hard to obtain from a particle or even a small molecule. If a pulsed laser is used, photons of scattered light appear in coincidence with the pulse of the light source, whereas luminescence photons mostly appear some nano-seconds later. This time difference is used, inter alia, for calculating the fluorescence lifetime. If a constant light source is used, however, as is mostly the case in FCS, there is no such possibility.

In Tellinghuisen et al. ("Analysis of Fluorescence Lifetime Data for Single Rhodamine Molecules in Flowing Sample Streams", Analytical Chemistry 66, No. 1, 64–72, 1994), a method of fluorescence lifetime spectroscopy is described which serves to filter the photons derived from the light source, i.e., a laser in this case, from the overall signal. To achieve this, the signal counter current is compared with the trigger signal, i.e, the excitation pulse of the pulsed laser. If a photon arrives simultaneously with the excitation pulse, considering the velocity of light, it is identified as a scattered light pulse and deleted. One drawback of this method is that detector pulses which are not generated simultaneously with the excitation pulse are not recognized. Examples thereof include dark currents in the detector. In addition, fluorescence photons, if coinciding with the excitation pulse within the limits of time resolution of the trigger signal, are also deleted. This may lead to inacceptable distortions in the subsequent signal processing. When relaxation signals are measured, as with fluorescence lifetime, there is an additional drawback in that the strongest portion of the signal is deleted, resulting in a dramatic deterioration of the signal-to-noise ratio.

Keller et al. ("Single-Molecule Fluorescence Analysis in Solution", Applied Spectroscopy 50, No. 7, 12A–32A, 1996) describes another method for determining the fluorescence lifetime. In this method, the time intervals between successive impulses arriving at the detector are determined by counting the number of trigger pulses, generated with 100 kHz, between two successive photons. These counts are stored in successive channels of a multichannel scaler (MCS). Then, this MCS signal is subjected to a temporal fast Fourier transformation (FFT) for smoothing. If, after FFT, at least 5 time intervals of the smoothed signal are below a visually determined threshold, the signal is considered coherent for the entire period of time during which the time intervals are continuously below the visually determined threshold, and rated as a fluorescence fraction, for some time called "burst" in scientific usage. Then, the thus filtered signal is evaluated with respect to fluorescence lifetime. However, the authors only use signal fractions in which more than 25 time intervals are below the visually determined threshold.

Disadvantages of the method described include the delayed evaluation and the limitation of the measuring time. The FFT, which is used and necessary for smoothing the data, is evaluated through a period comprising $2^n$ measuring points, the measuring points having to be present in a memory, MCS in this case, because of the mathematical method used in FFT. Only after FFT and a "visual" decision procedure, an assignment of the impulses can be made. For measurements in which counts of far less than 100 per millisecond occur, such a method may still be performed at low concentrations of the fluorescing particles (<<1 particle per measuring volume element).

However, in addition to determining the fluorescence lifetime, there are more methods for evaluating optical raw signals. These include autocorrelation and/or cross-correlation. The goodness of a correlation analysis is known to depend on the number of photons recorded per particle and per unit time in a linear or stronger than linear way. In a commercial FCS instrument, such as ConfoCor®, up to about 800 photons per millisecond is detected from a single molecule of Rhodamine 6G fluorescent dye. Even more photons are detected if several luminophors are present on or in the same particle, as is the case with vesicles, for example. In such cases, the method described by Keller et al. cannot be practised with acceptable expenditure, even when the most advanced electronics is used.

With an unsmoothed signal, it is not possible to use the falling below a threshold of the interval between the individual pulses as an evaluation criterion repeatedly if variations in the optical raw signal cause the intervals to be sporadically exceeded.

Both the methods described in Tellinghuisen et al. and those described in Keller et al. fail if a signal fraction specific of a class of particles is to be separated not only from the background, but also from at least one other signal fraction specific of a class of particles, as is the case, for example, with the reaction product and the excess component described above. The excess component also emits a shower of luminescence photons. A simple reduction of the overall signal by the fraction derived from scattered light or the use of a limit for the pulse width density does not achieve the object of the present invention.

It has been the object of the present invention to provide a method which allows to differentiate or detect particles in samples which contain at least two classes of particles.

The object of the invention is achieved by a method with the features of claim 1. Claims 2 to 18 relate to preferred embodiments of the method according to the invention.

According to the invention, the differentiation or detection of particles in a sample in which several classes of particles may be present is effected by identifying signal segments of time-resolved, optical raw signals from the sample on the basis of single photon detection (single pulse detection), wherein the sample contains at least two classes of particles;

the sample is illuminated by a light source;

the optical raw signals emitted by the sample, which are derived from at least one measuring volume element V, $V \leq 10^{-12}$ l, are detected with at least one detector unit;

at least one particle generates a signal fraction during its residence in the measuring volume element;

a signal segment of the optical raw signals is determined by the particle's actively and/or passively entering and then leaving again the measuring volume element;

the optical raw signals are segmented into arbitrary segments;

at least one set of statistical data based on the optical raw signals is established for at least one arbitrarily chosen segment; and said at least one set of statistical data or at least one combination of several sets of statistical data is evaluated for the presence of features characteristic of the signal fraction from at least one class of particles.

Within the meaning of the invention, the evaluation of said at least one set of statistical data or at least one combination of several sets of statistical data may also be done on the basis of features which are suspected to be characteristic of the signal fraction from at least one class of particles.

The following Figures illustrate the method according to the invention.

The ratios shown in the Figures relate to measurements of Rhodamin 6G labeled EGF (epidermal growth factor; 10 nM in aqueous solution) and EGF receptor bearing vesicles (7.5 nM).

Figure 1:
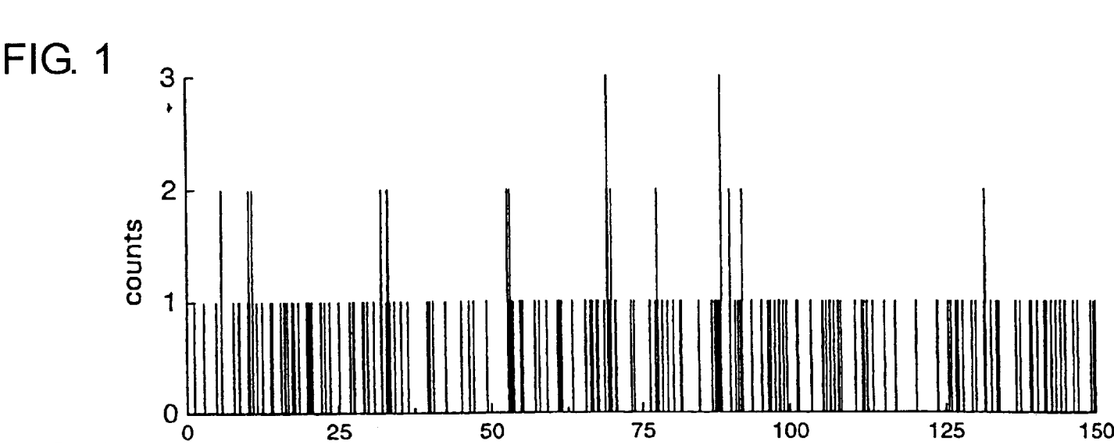
FIG. 1 shows e optical raw signal. Signals were detected as a function of time.
Figure 2:
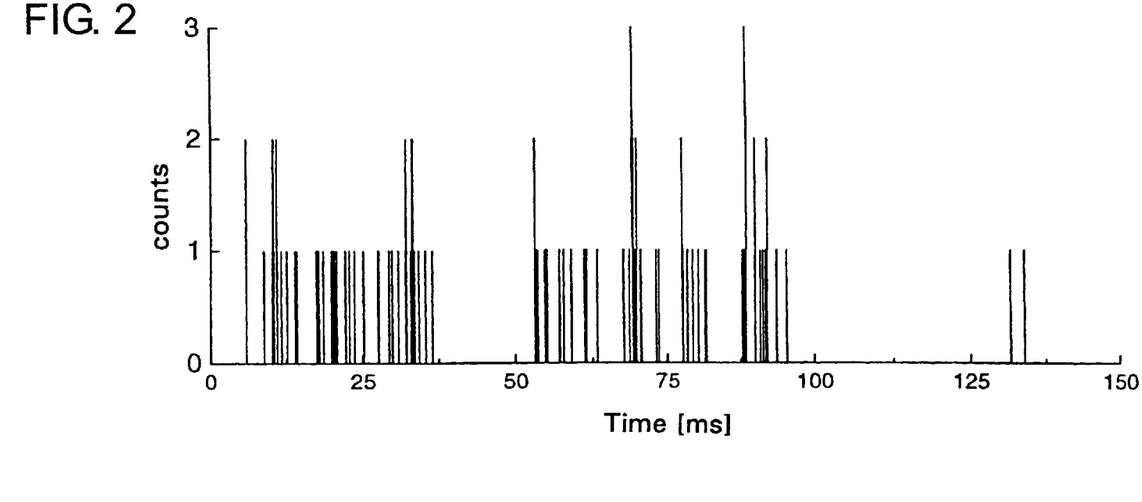
FIG. 2 shows a selection of those segments for which a set of statistical data is to be established.
Figure 3:
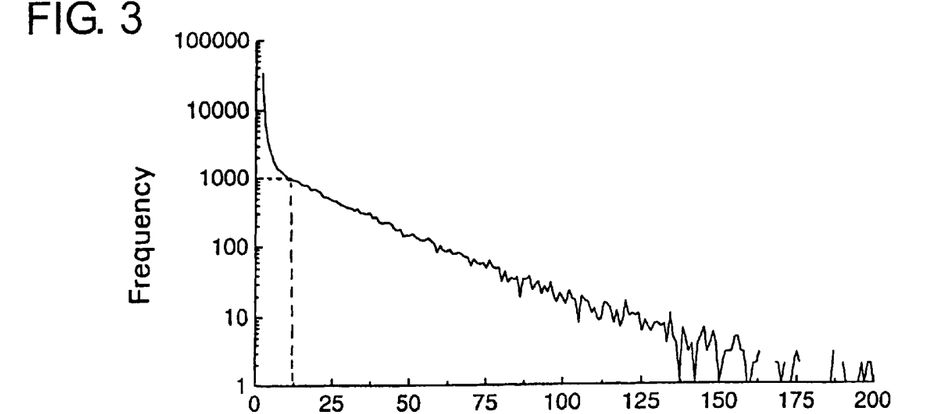
FIG. 3 shows a frequency distribution of the number of photons occurred in the segments. It can be estimated from the diagram t at about 12 photons occurred about 1,000 times.
Figure 4:
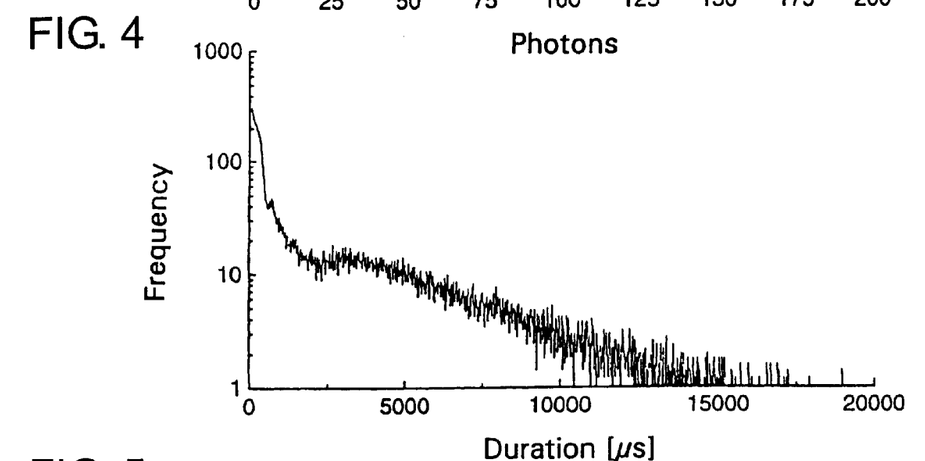
FIG. 4 shows a frequency distribution of the length of the segments in time (see FIG. 2).
Figure 5:
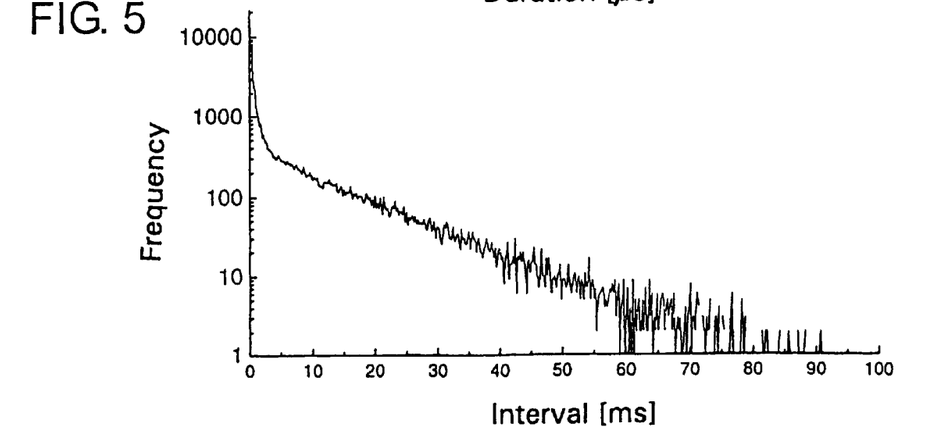
FIG. 5 shows a frequency distribution of the time intervals between the segments (see FIG. 2).
Figure 6:
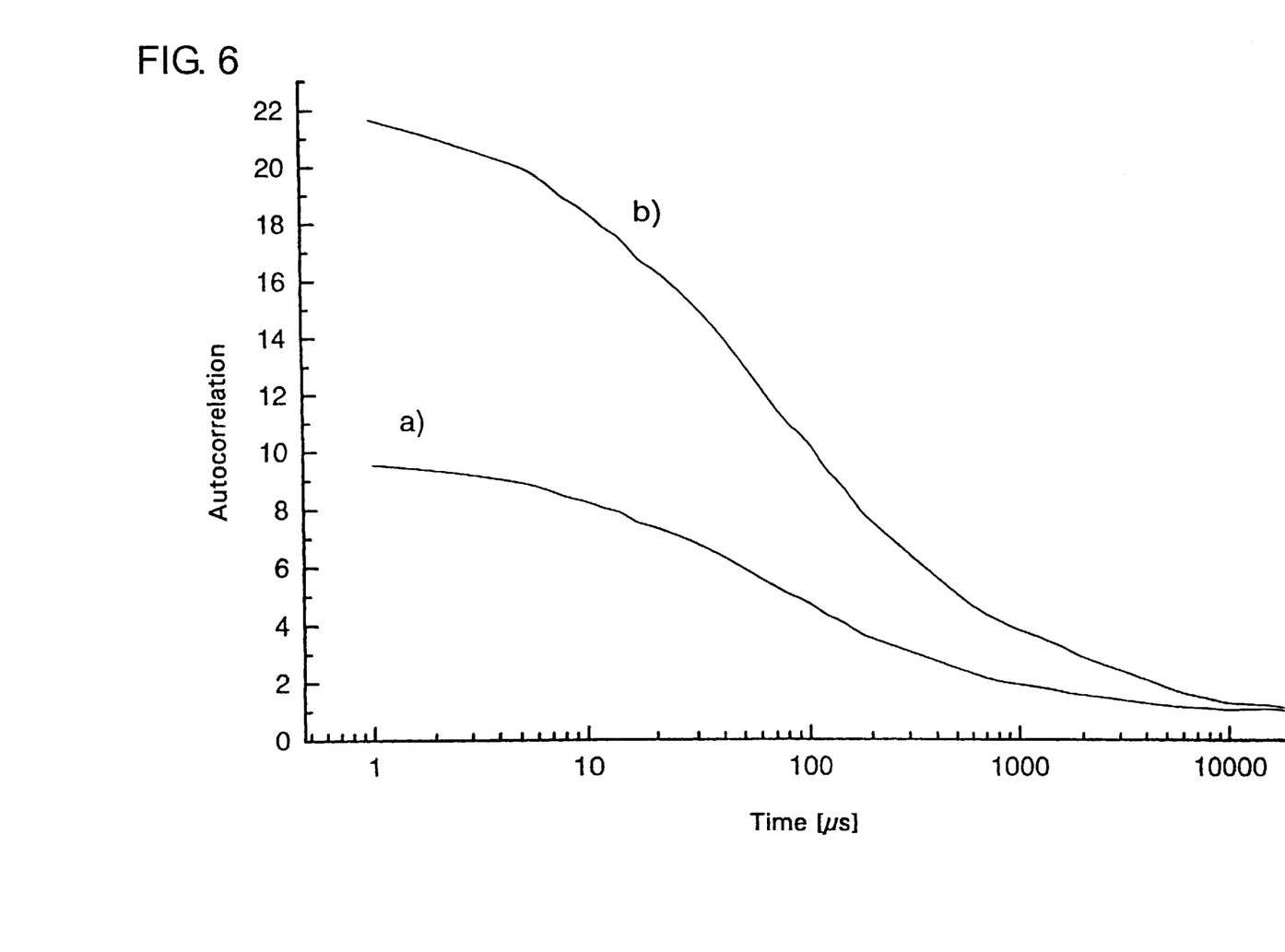
FIG. 6 shows a comparison between the autocorrelation functions of the optical raw signal (a) and the signal processed according to the invention (b).

According to the invention, at least one set of statistical data is established on the basis of the optical raw signals, this approach having the particular advantage that a reliable evaluation may be made despite of statistical fluctuations in the optical raw signal. This is in contrast to simple threshold decisions.

It may be desirable to form at least one auxiliary signal which can be derived from the optical raw signal, in particular, by a function and which is preferably in a temporally causal relationship with the optical raw signal. It may be preferable for the auxiliary signal and, in particular, its respective value to represent statistical information about at least one segment or subsegment of the optical raw signal at particular, all or almost all times. It may be desirable that such statistical information be superimposed on a basic signal fraction, or the statistical information be represented by a combination of auxiliary signals.

It may be desirable that at least one auxiliary signal be subjected to increments or decrements of a particular size or of a size which may depend, inter alia, on the current value or previous values of the auxiliary signal or the optical raw signal itself, for arbitrary pulses in the optical raw signal, especially for each photon detected.

It may further be desirable that such auxiliary signal be increased or decreased by a constant period of time which has been predetermined or which may be dependent, inter alia, on the current value or previous values of the auxiliary signal or the optical raw signal itself. In particular, such increase or decrease may be linear or exponential.

In another embodiment of the method according to the invention, the amplitude of this auxiliary signal is limited by an upper and/or lower limit, especially by cutting off. It is further possible to effect an appropriate modification of the size of the increment or decrement and/or the constant period of time, especially depending on the current value or previous values of the auxiliary signal, to limit the amplitude.

It may be preferred to consider in the evaluation whether at least one auxiliary signal within the segment or at the segment boundary reaches, exceeds or falls below a threshold. In one embodiment, this may be the only evaluation criterion if the auxiliary signal contains statistical information based on the optical raw signals for at least one segment or subsegment.

It may be desirable that the type of the statistical information represented by the auxiliary signals or its way of coding be variable along the time axis and, in particular, depend on the previous or current values of the same or at least one other auxiliary signal, or on at least one segment or subsegment length. It may be desirable that the evaluation be done on the basis of the statistical information represented by at least one auxiliary signal.

It may be preferred to define the segment boundary by marking, especially using an auxiliary signal, or by storing the times or a pulse number or photon number. Thus, in particular, segments may be defined which are subsequently subjected to evaluation. It may further be preferred to delete the segment mark, especially the mark at the beginning of a segment, afterwards. This may be done, in particular, with segments which are to be left unconsidered in a subsequent evaluation.

In one embodiment, the set of statistical data may be established in an intentionally or unintentionally distorted form, especially in an approximate form.

In another embodiment, the statistics may be implicitly contained in collected data.

According to the invention, at least one set of statistical data based on the optical raw signals is established for at least one arbitrarily chosen segment. In the case of several arbitrarily chosen segments, at least one set of statistical data based on the optical raw data may be established for them. Thus, for example, a set of statistical data for the burst durations may be established for several segments.

However, several segments may also be combined according to the invention, so that at least one set of statistical data based on the optical raw data can subsequently be established for the combined segments.

In one embodiment, the combination of several segments may be done by combining the statistical data for the individual segments.

In a further embodiment, the combination of several segments may be done by a temporal lining up of the segments, especially before a set of statistical data is derived from the combined signal or before it is subjected to an optional subsequent evaluation. It may be desirable to insert filling signal segments in the combined signal.

It may be preferred for the filling signal segments to have a fixed length, or that their lengths are selected such that the individual segments in the combined signal are in the same temporal relationship with one another as in the optical raw signal.

It may further be preferred to use a zero signal, i.e., no detected photons, or a signal typical of the presence or especially the absence of at least one class of particles in the measuring volume element as the filling signal.

It may further be preferred to use a signal derived from the optical raw signal, especially by filtering, as the filling signal.

It may be preferred to form segments of equal or different lengths, especially immediately successive or overlapping segments, when the optical raw signal is segmented.

It may further be preferred to effect the segmentation of the optical raw signals, and/or a possible selection of those segments for which a set of statistical data is to be established, on the basis of at least one function of the optical raw signal. In particular, at least one of those functions of the optical raw signal may form an auxiliary signal which is preferably in a temporally causal relationship with the optical raw signal.

It may be preferred to segment the optical raw signal at those times where at least one auxiliary signal reaches, exceeds or falls below at least one threshold. Segmentation may further be made in the neighborhood of such times.

It may be desirable to select segments for establishing a set of statistical data depending on whether at least one auxiliary signal reaches, exceeds or falls below at least one threshold in the respective period of time. It may further be desirable to make a selection according to the length of such segments.

It may further be desirable for the segments to be increased or decreased by certain periods of time at the beginning and/or at the end thereof, wherein said periods of time may be, in particular, predetermined or dependent on the segment length and/or features of the optical raw signal and/or the auxiliary signal, especially within the respective segment and/or the neighboring ranges.

In another embodiment, it may be preferred that the segmentation of the optical raw signals, the establishing of the set of statistical data and the evaluation are effected in a cyclic process.

It may be desirable that exactly one segment of the optical raw signal be considered in each cycle.

Especially in this case, it may be preferred that at least one segment is repeatedly modified, especially divided, combined with another segment, shifted, decreased or increased. In particular, said shifting, increase or decrease may be by a particular constant period of time, an infinitesimally small period of time, or up to, up to shortly before or up to shortly behind the pulse of the optical raw signal or detected photon next to a segment boundary. This procedure may also be preferred for subjecting at least one segment to a subsequent evaluation.

It may be desirable that at least one segment is replaced in the subsequent cycle by another, especially a successive, segment, in particular, by an infinitesimally small segment, a segment having a particular length or a segment containing a particular number of pulses of the raw signal or detected photons.

If the segmentation, establishing of the set of statistical data and evaluation are effected in a cyclic process, it may be desirable that at least one segment which is optionally assigned to at least one class of particles and/or subjected to at least one optional subsequent evaluation is determined only in the last, in several or in all cycles.

Especially for accelerating the method, at least one set of statistical data and/or its evaluation for at least one segment or subsegment may be derived from at least one set of statistical data and/or its evaluation for at least one other segment. This may be preferred, in particular, for overlapping segments. Especially in a cyclic modification of segments, it may be desirable that at least one set of statistical data and/or its evaluation from a preceding cycle, especially from the previous cycle, be used in said derivation.

In a preferred embodiment, at least part of the basis of the evaluation for at least one set of statistical data for a segment may be constituted by the set of statistical data for at least one other segment, especially a neighboring segment or a segment which is increased or decreased with respect to the segment to be evaluated.

In such a cyclic process, it may be preferred that the evaluation only in at least one cycle is performed according to features which are typical of the presence of at least one class of particles. In particular, it may be desirable to omit the evaluation and optionally even the establishing of the set of statistical data in part of the cycles.

It may be preferred to pass the cycle once or several times.

It may further be preferred to stop the cyclic modification of at least one segment in a cyclic process or to change the kind of modification when at least one auxiliary signal reaches, exceeds or falls below a threshold.

In a preferred embodiment, the optical raw signals are not physically segmented, but the segmentation is defined by the fact that at least one set of statistical data is established which is based on at least one segment.

It may be preferred to effect the segmentation on the basis of the optical raw signal, especially to form segments containing a constant number of pulses of the optical raw signal or of detected photons. In particular, if the segmentation is cyclically repeated, it may be preferred to initially select a segment which contains just one pulse or one detected photon.

It may further be preferred to use simple heuristics for segmenting the optical raw signal and selecting the segments for the set of statistical data. In particular, it may be preferred to preliminarily discard segments which are evidently unsuitable for differentiating or detecting at least one class of particles.

In another embodiment, the method according to the invention may be partially or wholly incorporated in computer hardware, especially using ASICs or FPGAs.

In another preferred embodiment, the method may be performed in real-time operation, which is of particular advantage especially for applications in the field of the so-called high-throughput screening of pharmaceutically active substances.

According to the invention, the photons are detected individually (single photon count or single pulse count). The recording of the counter pulses can be effected in various ways. Thus, for example, the time of registration by the detector may be assigned to every single pulse recorded, or else the number of individual pulses recorded in a given period of time can be established. It may be preferred to record the individual pulses on several detectors and/or to record further signals in parallel which are in a physical relationship with the individual pulses recorded and thus provide additional information.

The photons are emitted by particles which enter the measuring volume element V, with $V \leq 101^{-12}l$, and leave it again. A particular advantage of the small measuring volume element is to be seen in the fact that even at concentrations in the nanomolar range, only a few particles are present in the measuring volume element. This effect becomes particularly clear for larger particles, such as cellular membrane fragments or vesicles, which can be prepared at most in the picomolar range of concentrations. To be able to perform a homogeneous assay, e.g., of the binding of dye-labeled ligands to receptors in membrane fragments, at such concentrations, the ligand concentration must be chosen to be a significant excess. This means that only free ligands are present in the measuring volume element for the better part of the measuring time, and the reaction product in the form of ligand-binding membrane vesicles is rarely found. However, during the residence of the membrane vesicle in a small measuring volume element, its signal fraction dominates over the recorded optical raw signal at suitably selected concentrations, so that the signal fractions from the free ligand and free dye classes of particles can in a first approximation be neglected in comparison. In a second approximation, it may be preferred to consider them in the evaluation of the signal segment. In contrast, in a larger measuring volume element, there are always both free ligands and free dyes, and membrane fragments. In this case, as a consequence of the fact that a mean value of several particles is recorded, both signal fractions are almost equal in any segments so taht an identification of the various signal fractions according to classes of particles would no longer be possible.

The small measuring volume element alone is not sufficient for identifying the signal segments if more than one class of particles is present in the sample, and the identification is only effected through the threshold decisions described in the literature. Background signals, such as the noise of the detector, or the Raman signal of the solvent, which is always present in a high concentration, even in a small measuring volume element, result in a uniform signal against which any burst is clearly recognized and can be identified though simple threshold decisions. If more than two classes of particles are present in the measuring volume element, both are recognized as bursts without any difference. Only the establishing of a set of statistical data for at least one segment or subsegment based on the optical raw signals according to the invention enables the particles to be differentiated or detected by more than one class of particles.

In one embodiment of the method according to the invention, the particles of at least one class of particles are luminescent and/or labeled with at least one luminophor. The particles of a class of particles may be, in particular, molecules, macromolecules, viruses, bacteria, cells, beads, vesicles, particle fluids, molecular aggregates or complexes. One class of particles may comprise several types of particles. For example, when the binding of a labeled ligand to receptors on vesicles is measured, free luminophors are frequently still present in the sample. In this case, it is desirable to differentiate the signal segments in which a signal fraction derived from receptor-bound ligands is contained from the remainder of the optical raw signal. Accordingly, vesicles would be included among one class of particles, and labeled free ligands and free luminophors among another. It is to be pointed out that a class of particles may altogether contain a whole distribution of, e.g., particle sizes, as is often the case with membrane fragments or vesicles. In particular, different types of particles belong to different classes of particles if such different types of particles are differentiated in the identification of the signal segments and/or in the optional subsequent evaluation.

At least two classes of particles are present in the sample the particles of which enter the measuring volume element, in particular, at unpredictable times and leave it again at unpredictable or predictable times.

According to the invention, a set of statistical data is established on the basis of the optical raw signals for at least one arbitrarily chosen segment. In a preferred embodiment, this may be the establishing of a set of statistical data for the number of individual pulses and/or the time intervals between the individual pulses, especially the characteristic triplet time distribution and/or triplet frequency of the luminophors and/or the elastically and/or inelastically scattered light.

For example, the frequency and the residence time of a luminophor in the triplet state depends on its chemical environment. The latter often changes when the labeled particle is bound to another particle, and is thus suitable for identifying such binding.

The scattering of the excitation light is another example of an identification according to classes of particles. Free ligands hardly produce any scattered light; in contrast, larger particles, such as membrane fragments or beads, produce so much that their signal is detectable. The intensity of the scattered light can even be used for the calibration of other, e.g., luminescence, signals with respect to the size of the particles. This approach significantly contributes to a more precise determination of the binding constant. In the example of the membrane fragments and labeled ligands, the density of receptors per membrane area can even be concluded from the statistics of the size of the membrane fragments and the recorded individual pulses when the concentration of the ligands is appropriately selected. This size is of great practical importance in research and otherwise hardly accessible to experimental determination. Instead of the scattered light, the luminescence of a second luminophor which becomes incorporated in the membrane without interacting with the ligand may also be used.

It may be preferred to select the type of set of statistical data and/or combination of more than one set of statistical data depending on the type of class of particles to be identified and its characteristical features.

The following example may illustrate this approach. As in the example mentioned above, the classes of particles of a homogeneous assay may again be receptor-bearing vesicles, on the one hand, and free luminescent or luminescence-labeled ligands which will bind to the receptors to a certain percentage according to an equilibrium constant. Free ligands which move through the measuring volume element will produce relatively short bursts of high intensity on average whereas vesicles, due to their low diffusion rate, will produce relatively long ones on average. A simple threshold decision as described in the literature, which evaluates whether individual pulses are repeatedly recorded within a predefined short period of time, would not be sufficient for identification. When the threshold is set too low, both classes of particles will be counted together, and when the threshold is higher, the threshold criterion is hardly ever met since pauses also keep occurring with the vesicles due to statistical fluctuations.

Only the establishing of a set of statistical data, e.g., for the quantity $I(\Delta t)I(\Delta t+t_1) I(\Delta t+t_2) I(\Delta t+t_3)$ with the number I of individual pulses respectively counted during the intervals $\Delta t$, $\Delta t+t_1$, $\Delta t+t_2$, $\Delta t+t_3$, with appropriately selected constants $t_i$ with i=1, 2, 3, yields a statistically reliable characteristic by which the classes of particles can be differentiated.

It may be preferred to illuminate the sample with polarized excitation light and to establish a set of statistical data for polarization.

For example, when two detectors with crossed polarization filters are used, a set of statistical data for the mutual ratio of counted individual pulses can be established.

In another embodiment, it is possible to illuminate the sample with pulsed or temporally modulated excitation light and to establish a set of statistical data for the time intervals to the individual pulses from the excitation pulses or from the phase of the excitation light.

A parallel operation of the photon recording is also conceivable, e.g., luminescence at different wavelengths, or the additional recording of scattered or Raman light, or any combination of these parameters.

In a further embodiment, it may be desirable to assign segments and/or portions of said segments of the optical raw signals and/or of the already established at least one set of statistical data to at least one class of particles, and further to classify and subject them to at least one evaluation for determining chemical and/or physical parameters which are specifically of said at least one class of particles. The evaluation may be done in the form of time-averaging, and/or the determination of higher statistical moments, and/or the determination of the auto- and/or cross-correlation, and/or Fourier transformation, and/or analysis of a distribution function of the optical raw signals of the (sub)segments and/or the length of the (sub)segments and/or luminescence depolarization and/or luminescence lifetime.

It may be preferred to subject the lengths of the bursts from the at least one class of particles and its corresponding set of statistical pulse data to another statistical evaluation after classification.

In a preferred embodiment, the luminescence of two spectrally different luminophors is measured with two detectors in parallel, for example, in an arrangement as described in WO 94/16313. The method according to the invention in combination with cross-correlation as a further step of evaluation after the classification of the optical raw signal particularly benefits from the classification, since correlations can be better determined after the application of Boolean functions, such as "AND", and/or "NAND". Above all, a correlation can be determined from the presence of exclusively one color in the measurement volume element, which is not possible by any other known method.

In particular, it is possible to determine cross-correlations and/or other dependent statistics also with only one detector. For suitable optical raw data, the statistics allow to decide whether the segment is to be assigned to only one or to more classes of particles. For example, if exactly two classes of particles, A and B, are differentiated, classification may be made according to the three cases: only A; only B; and both A and B. In this example, it may even be preferred to distinguish yet a fourth class: neither A nor B.

In another embodiment of the method according to the invention, the light source and the detector unit are confocally arranged with respect to the measuring volume element.

In some applications, it may be preferred to stimulate the luminescent or luminophor-labeled particles to emission by two-photon excitation.

Another embodiment is characterized in that the light passes a means which is transparent to the corresponding wavelength of the light and/or the light emitted by the sample, which means is provided between the light source and the sample and/or between the sample and the detector unit, in close proximity of the sample, and has at least one region the largest dimension of which in at least one direction of space is smaller than the wavelength of the light and/or the light emitted by the sample. Further details are described in WO 96/13744.

In another embodiment, the method according to the invention is combined with the method described in the European patent Application 96 116 373.0, the disclosure of which is incorporated herein by reference.

If the diffusion of the particles of at least one class of particles is highly restricted, it may be preferred to produce a forced movement of the sample and the measuring volume element contained therein (e.g., by vibration or flow) and/or a continuous or discontinuous change of the space coordinates of the measuring volume element within the sample. This is preferably done by changing the focus and/or changing the position of the illuminated volume element. Further details are described in WO 94/16313.

In a preferred embodiment, the change of the space coordinates is recorded in parallel with the individual pulses and/or calculated from parameters of the equipment. It may be used in establishing said at least one set of statistical data based on optical raw signals for said at least one segment and/or subsegment. For example, for a periodic or quasi-periodic movement in which the measuring volume is found at the same location within the sample at least twice during measurement, said at least one segment and/or subsegment can be used for the same statistics.

In another embodiment, the molar concentrations of the particles to be differentiated vary by a factor of more than 10.

It may further be preferred to determine the chemical and/or physical properties of the surface of at least one particle using luminescence properties. In particular, the density of the receptors per membrane area can be determined.

What is claimed is:

1. A method for differentiating or detecting particles in a sample in which several classes of particles may be present by identifying signal segments of time-resolved, optical raw signals from the sample on the basis of single photon detection (single pulse detection), wherein
   the sample contains at least two classes of particles;
   the sample is illuminated by a light source;
   the optical raw signals emitted by the sample, which are derived from at least one measuring volume element V, $V \leq 10^{-12}$l, are detected with at least one detector unit;
   at least one particle generates a signal fraction during its residence in the measuring volume element;
   a signal segment of the optical raw signals is determined by the particle's actively and/or passively entering and then leaving again the measuring volume element;
   the optical raw signals are segmented into arbitrary segments;
   at least one set of statistical data based on the optical raw signals is established for at least one arbitrarily chosen segment; and
   said at least one set of statistical data or at least one combination of several sets of statistical data is evaluated for the presence of features characteristic of the signal fraction from at least one class of particles.

2. The method according to claim 1, characterized in that particles of at least one class of particles are luminescent and/or labeled with at least one luminophor.

3. The method according to claim 1, characterized in that particles of a class of particles are molecules, macromolecules, viruses, bacteria, cells, beads, vesicles, particle fluids, molecular aggregates or complexes.

4. The method according to claim 1, characterized in that a set of statistical data is established for the number of individual pulses and/or the time intervals between the individual pulses, especially the characteristic triplet time distribution and/or triplet frequency of the luminophors and/or the elastically and/or inelastically scattered light.

5. The method according to claim 1, characterized in that the sample is illuminated with polarized excitation light and a set of statistical data for polarization is established.

6. The method according to claim 1, characterized in that the sample is illuminated with pulsed or temporally modulated excitation light and that a set of statistical data is established for the time intervals to the individual pulses from the excitation pulses or from the phase of the excitation light.

7. The method according to claim 1, characterized in that segments and/or portions of said segments and/or of the at least one established set of statistical data are assigned to at least one class of particles.

8. The method according to claim 1, characterized in that said segments and/or portions of said segments and/or of the at least one established set of statistical data, after having been assigned to at least one class of particles, are classified and subjected to at least one evaluation for determining chemical and/or physical parameters which are specifically of said at least one class of particles.

9. The method according to claim 1, characterized in that said evaluation is done in the form of time-averaging, and/or the determination of higher statistical moments, and/or the determination of the auto-and/or cross-correlation, and/or Fourier transformation, and/or analysis of a distribution function of the optical raw signals of the (sub)segments and/or the length of the (sub)segments and/or luminescence depolarization and/or luminescence lifetime.

10. The method according to claim 1, characterized in that, after classifying the optical raw signal and/or the at least one established set of statistical data, said at least one classified signal is evaluated by at least one Boolean function and then optionally subjected to further evaluation.

11. The method according to claim 1, characterized in that a confocal arrangement of the light source and the detector unit with respect to the measuring volume element is used.

12. The method according to claim 1, characterized in that said luminescent or luminophor-labeled particles are stimulated to emission by two-photon excitation.

13. The method according to claim 1, characterized in that the light passes a means which is transparent to the corresponding wavelength of the light and/or the light emitted by the sample, which means is provided between the light source and the sample and/or between the sample and the detector unit, in close proximity of the sample, and has at least one region the largest dimension of which in at least one direction of space is smaller than the wavelength of the light and/or the light emitted by the sample.

14. The method according to claim 1, characterized in that the space coordinates of the measuring volume element are changed relatively to the space coordinates of the sample during measurement to measure stationary or very slowly diffusing luminescent or luminescence-labeled particles.

15. The method according to claim 1, characterized in that said change of the space coordinates is recorded in parallel with the optical raw signals and considered in establishing said at least one set of statistical data, especially for periodic or quasi-periodic changes of the space coordinates.

16. The method according to claim 1, characterized in that the molar concentrations of the particles to be differentiated vary by a factor of more than 10.

17. The method according to claim 1, characterized in that the chemical and/or physical properties of the surface of at least one particle are determined using luminescence properties.

18. The method according to claims 1, characterized in that the density of receptors per membrane area is determined.

19. A method for differentiating or detecting particles in a sample in which several classes of particles may be present by identifying signal segments of time-resolved, optical raw signals from the sample on the basis of single photon detection (single pulse detection), wherein the sample contains at least two classes of particles;

the sample is illuminated by a light source;

the optical raw signals emitted by the sample, which are derived from at least one measuring volume element V, $V \leq 10^{-12}$l, are detected with at least one detector unit;

at least one particle generates a signal fraction during its residence in the measuring volume element;

a signal segment of the optical raw signals is determined by the particle's actively and/or passively entering and then leaving again the measuring volume element;

the optical raw signals are segmented into arbitrary segments;

at least one set of statistical data based on the optical raw signals is established for a plurality of segments chosen from among said arbitrary segments, and said at least one set of statistical data or at least one combination of several sets of statistical data is evaluated for the presence of features characteristic of the signal fraction from at least one class of particles.

* * * * *